United States Patent [19]

Katakura

[11] Patent Number: 5,040,537
[45] Date of Patent: Aug. 20, 1991

[54] METHOD AND APPARATUS FOR THE MEASUREMENT AND MEDICAL TREATMENT USING AN ULTRASONIC WAVE

[75] Inventor: Kageyoshi Katakura, Tokyo, Japan

[73] Assignee: Hitachi, Ltd., Tokyo, Japan

[21] Appl. No.: 273,570

[22] Filed: Nov. 21, 1988

[30] Foreign Application Priority Data

Nov. 24, 1987 [JP] Japan .................................. 62-294069
Apr. 13, 1988 [JP] Japan .................................. 63-89048

[51] Int. Cl.$^5$ ............................................. A61B 1/00
[52] U.S. Cl. ............................. 128/630; 128/24 AA; 128/662.02; 604/890.1
[58] Field of Search ..................... 128/660.05, 660.07, 128/661.08, 661.09, 662.02, 24 AA, 24 EL, 630, 660.03; 606/127, 128

[56] References Cited

U.S. PATENT DOCUMENTS

| | | | |
|---|---|---|---|
| 4,265,251 | 5/1981 | Tickner | 128/662.02 |
| 4,276,885 | 7/1981 | Tickner et al. | 128/662.02 |
| 4,442,843 | 4/1984 | Rasor et al. | 128/662.02 |
| 4,572,203 | 2/1986 | Feinstein | 128/662.02 |
| 4,622,978 | 11/1986 | Matsuo et al. | 128/660.05 |
| 4,630,612 | 12/1986 | Uchida et al. | 128/660.05 |
| 4,669,472 | 6/1987 | Eisenmenger | 128/24 A |
| 4,685,461 | 8/1987 | Forssmann et al. | 128/24 A |

FOREIGN PATENT DOCUMENTS 0052575 1/1986 European Pat. Off. .

OTHER PUBLICATIONS

Meltzer et al., *The Source of Ultrasound Contrast Effect*, J. Clin. Ultrasound, 8:121–127, Apr. 1980.

*Primary Examiner*—Lee S. Cohen
*Assistant Examiner*—John D. Zele
*Attorney, Agent, or Firm*—Antonelli, Terry, Stout & Kraus

[57] ABSTRACT

An ultrasonic measuring apparatus and method operating as an ultrasonic echocardiograph and a doppler blood flow speed meter by creating numerous microbubbles as a contrast medium or reflector only in an intended blood vessel. The apparatus comprises an injector which injects into a vein of patient an agent which is a substance encapsulated in numerous microcapsules of several micrometer or less in diameter and distributed in a carrier liquid so that it produces microbubbles through the reaction with blood, and a shock wave transmitter which emits a shock wave with the dominant positive pressure from the body surface toward a specific blood vessel such as the root of the aorta so that only microcapsules in the specific blood vessel, among all dispersed in the whole body, are broken by the shock wave and the agent is released in the blood flow.

21 Claims, 2 Drawing Sheets

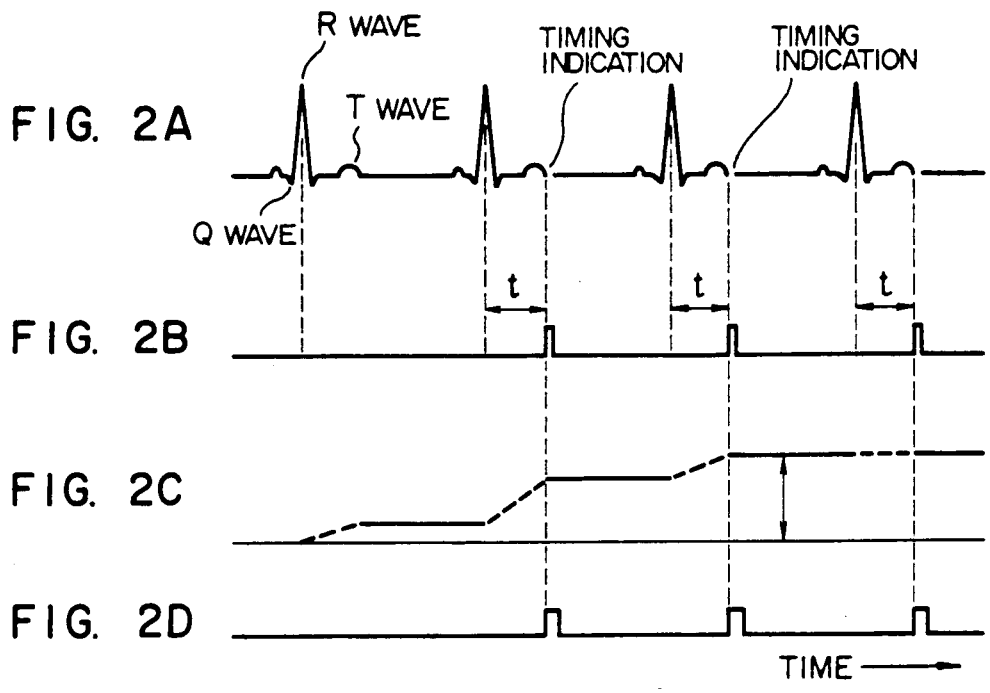
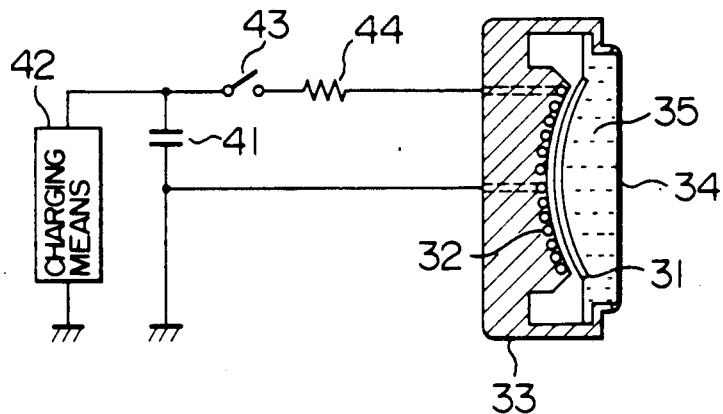
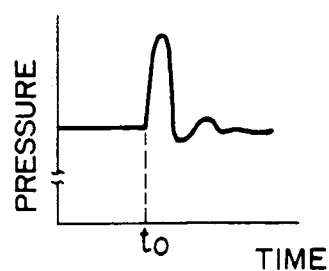

a liquid in a state of emulsion. The fine capsules or integrated particles have such a size that they can penetrate capillaries. After numerous capsules or integrated particles introduced to vein blood have encircled the patient's body and reached a proper position, they are broken by the application of a shock wave and the agent is dispersed in the blood.

METHOD AND APPARATUS FOR THE MEASUREMENT AND MEDICAL TREATMENT USING AN ULTRASONIC WAVE

BACKGROUND OF THE INVENTION

This invention relates to a diagnostic technique for imaging the shape of a specific blood vessel, e.g., coronary artery, and measuring the blood flow speed in the blood vessel, and also relates to the apparatus used for the treatment of the specific blood vessel.

It is known that the presence of numerous microbubbles in a liquid provides a pronounced imaging effect for the ultrasonic echography. For example, a method disclosed in U.S. Pat. No. 4,265,251 introduces into blood a solid precursor, typically saccharide compound, and numerous microbubbles produced when the saccharide has melted in blood are used for the echography of a selected part of a blood vessel. European patent Laid-open No. 0052575 describes the use of a blood-melted precursor similar to the above-mentioned one, but in the form of particles, each being integrated finer particles so that spaces among finer particles are filled with gas. Another method of U.S. Pat. No. 4,276,885 injects directly into the blood flow numerous microbubbles fixed by gelatin, thereby intensifying the ultrasonic image.

SUMMARY OF THE INVENTION

The conventional methods are either creating microbubbles in the blood flow under examination, or injecting microbubbles which have been created externally in advance into the blood flow under examination. However, neither of these methods are said to be appropriate for imaging only a specific blood vessel, particularly the coronary artery. The reason is that the injection through a vein causes the bubbles or precursor to reach peripheral blood vessels in the heart and lung before arriving at the coronary artery. Although an artery catheter for introducing bubbles or precursor to the root of the aorta enables the contrast medium to reach the coronary artery promptly, the use of the artery catheter is undesirable in many cases from the viewpoint of time and labor for the examination and the risk imposed on the patient.

Similar to the delivery of a contrast medium to the intended part of a blood vessel in ultrasonic imaging as described above, it is also difficult to deliver another agent, e.g., thrombus liquefacient, to the intended part, e.g., the end of the coronary artery, effectively by the introduction of the agent through a vein.

Accordingly, it is an object of this invention to provide a method and apparatus for delivering a contrast medium or other agent to an intended specific blood vessel effectively.

Depending upon the agent used, this invention is characterized in that the agent is packed in fine capsules which are breakable by shock wave pressure or packed among particles of integrated fine particles, with the fine capsules or integrated particles being distributed in a liquid in a state of emulsion. The fine capsules or integrated particles have such a size that they can penetrate capillaries. After numerous capsules or integrated particles introduced to vein blood have encircled the patient's body and reached a proper position, they are broken by the application of a shock wave and the agent is dispersed in the blood.

In accordance with the apparatus, this invention is characterized by means of injecting numerous fine capsules, with an agent being packed therein, into the patient's body, and means of applying a shock wave with a dominant positive pressure from outside of the body to the intended position so that only capsules, among all dispersed in the body, located in the intended position are broken selectively.

In the aspect of the effective introduction of agent to the coronary artery, the apparatus features the inclusion of means of detecting the heart beat and means of timing the generation of shock wave in relation with the heart beat.

BRIEF DESCRIPTION OF THE DRAWINGS

FIGS. 2A–2D are timing charts showing the timing of activation with respect to the heart beat; and FIGS. 3A and 3B are diagrams showing the arrangement of the shock wave transmitter and the waveform of sound pressure produced by it, respectively.

DESCRIPTION OF THE PREFERRED EMBODIMENT

Figure 1:
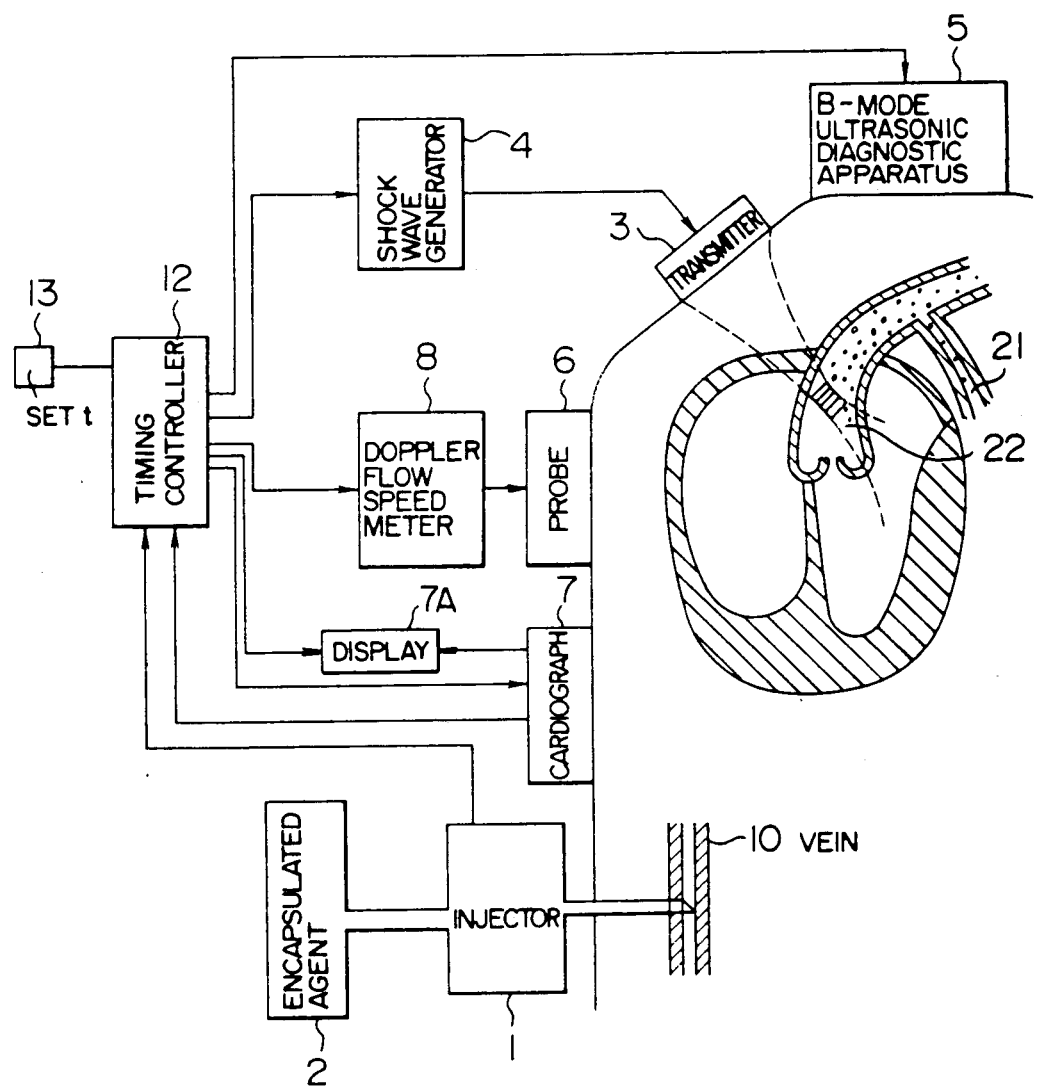
FIG. 1 is a block diagram showing an embodiment of the invention.

FIG. 1 shows the arrangement of the inventive apparatus which is intended for both the observation and treatment of the coronary artery. An injecting device 1 is used to inject an agent such as the contrast medium into the patient's body. The agent 2 supplied to the injecting device 1 consists typically of numerous particles of fine capsules made of fatty acid ester or lecithin, in which is contained a material such as hydrogen bicarbonate soda which produces gas when in contact with water, distributed in an aqueous carrier liquid such as physiologic salt solution in a state of emulsion. The size of particles is determined such that all particles can penetrate the pulmonary capillaries, and it is few micrometers in diameter at most. Typically, the particle diameter has a mean value of 1.9 $\mu$m, and 90° of particles have diameters of 3.0 $\mu$m or less. More preferably, all particles have diameters of 2.0 $\mu$m or less. Injected agent particles are dispersed in blood in the patient's body and delivered to the aorta by way of the right heart, lung and left heart.

A shock wave transmitter 3 emits a pulsative shock wave by being energized by a driver 4. In this embodiment, the transmitter 3 is positioned and directed so that the shock wave is emitted toward the root of aorta indicated by 22, with the intention of imaging the coronary artery indicated by 21 and measuring the blood flow speed in it. The agent particles which have reached the root of aorta are broken by being hit by the shock wave and the agent is released into the blood. Consequently, microbubbles are created in the blood and a number of them are introduced to the coronary artery.

A timing controller 12 operates on the driver 4 so that the shock wave is generated at a prescribed moment on the cardiogram of the patient's body presented by an electrocardiograph 7. FIGS. 2A–2D are timing charts used to explain this timing control. FIG. 2A shows the cardiographic waveform provided by the cardiograph 7. The systolic period of the heart begins at around the Q-wave of cardiogram and lasts until around the end of the T-wave, and thereafter the heart enters the diastolic period. Since artery blood is introduced into the coronary artery during the diastolic period of the heart, the most preferable timing of emitting the shock wave is between the end of the systolic period and the beginning of the diastolic period, in order to introduce microbubbles created at the root of aorta efficiently into the coronary artery. In addition, for the avoidance of premature beat, the shock wave must not be emitted at least in an end portion of the diastolic period.

In this embodiment, the timing controller issues a trigger signal for shock wave generation to the driver 4 upon expiration of a certain time length t following the R-wave on the cardiogram, as shown in FIG. 2B. The delay time t is set on a setting dial 13 in compliance with the heart beat period of the patient's body. After several heart beat periods following the injection of agent particles into the vein, the concentration of particles within the aorta rises as shown in FIG. 2C. The timing controller 12 counts heart beats following the commencement of agent injection by the injecting device 1 on the basis of the output of the cardiograph 7, and issues the trigger signal several times at each specified beat count.

The cardiograph 7 constantly displays the immediate cardiogram and also the time point of shock wave emission based on the timing display signal returned from the timing controller 12 on a display 7A. Specifically, the emission time point is displayed as a "cut" or break in the waveform of the cardiogram, as shown in FIG. 2A.

A B-mode an ultrasonic diagnostic apparatus emits a supersonic or ultrasonic wave and provides an ultrasonic echograph on the basis of the well-known sectorial ultrasonic scanning. The emission of shock wave creates numerous microbubbles in artery blood, and the bubbles in the coronary artery which serve as effective reflectors, intensify the echo image of the coronary artery. The agent dispersed in blood inside the heart and pulmonary capillaries still remains in particles, producing a weaker reflected sound wave as compared with that from bubbles, and therefore the resulting echograph has its image of only coronary artery intensified selectively.

Moreover, the presence of the high-reflective substance in blood inside the coronary artery enables the measurement of blood flow speed inside the coronary artery through the provision of a doppler flow speed meter 8. In this case, the position of coronary artery is detected from the echograph provided by the B-mode ultrasonic diagnostic apparatus 5 so that the probe 6 is positioned and directed properly, and the ultrasonic impulse beam is emitted to measure the doppler shift of the reflected wave. It should be noted that the measurement of blood flow speed in the circumflex coronary artery in the rear of heart is only feasible by the foregoing selective bubble generation.

The B-mode ultrasonic diagnostic apparatus 5 and doppler flow speed meter 8 are given an inhibit signal for the prevention of noise contamination in the resulting image and detected signal caused by the shock wave from the transmitter 4. The inhibit signal provided by the timing controller rises simultaneously with the shock wave trigger signal and falls after a certain time length. During the active period of the inhibit signal, the B-mode diagnostic apparatus 5 and doppler flow speed meter 8 are prohibited from writing to their internal display memories. Alternatively, the measuring operation of these instruments may be halted by the inhibit signal. In any case, the inhibit signal needs to last at least the time length in which the disturbing sound wave caused by the shock wave exists, and it is around 10 ms.

FIG. 3A shows a specific arrangement of the transmitter 3 and driver 4. The transmitter 3 has a structure, with a nonmagnetic, conductive diaphragm 31 being disposed in close proximity to a spiral coil 32. The diaphragm 31 is provided on its concave front side with a cover 34 so that liquid 35 for propagating the sound wave is held. Indicated by 33 is a frame for supporting the diaphragm, coil and cover, and the frame 33 has a sufficiently greater mass than the diaphragm. The transmitter is used in such a way that the cover 34 is brought in tight contact with the patient's body surface.

The spiral coil 32 is connected to a drive circuit which includes a capacitor 41, charging means 42, switch 43 and discharging resistor 44. The capacitor 41 is charged by the charging means 42 when the switch 43 is open, and it supplies a discharging current to the spiral coil 32 at the moment when the switch 43 is closed. The nonmagnetic, conductive diaphragm 31 responds to the current to emit a shock wave derived from the magnetic repellence force.

FIG. 3B shows on the time axis the sound pressure at the focal point of the diaphragm. When the switch is closed at $t_0$, the sound pressure rises sharply, and an impulse sound pressure with a dominant positive pressure is produced. The impulse sound wave with the dominant positive pressure causes less suffering and damage to the patient as compared with a sound wave with a dominant negative pressure, and the intended destruction of agent particles in the blood flow can be carried out safely.

In the foregoing embodiment, it is possible to display the cardiogram produced by the cardiograph 7, the ultrasonic echograph produced by the B-mode diagnostic apparatus 5, and the blood flow speed measured by the doppler flow speed meter 8 simultaneously on a single display unit with a proper separation provided on the screen. It is also possible to display the measured value of doppler flow speed meter in a color code on the ultrasonic echograph. Furthermore, the B-mode ultrasonic diagnostic apparatus 5 and doppler flow speed meter 8 may share a single probe on a time slice basis.

Although the agent used in the foregoing embodiment is a bubble-sourcing substance contained in particles of fine capsules which are distributed in a carrier liquid, it may be formed in particles, each being fine integrated particles, which are distributed in a carrier liquid. Such integrated particles disperse in the blood flow when hit by the shock wave, releasing gas which has been held in spaces among particles as bubbles, more quickly to release gas which has been captured in. The material of the agent is chosen such that it does not melt quickly in the blood while it is in the integrated state. The produced gas must be harmless for the human body, and it is preferably oxygen or carbon dioxide since it is absorbed in blood quickly.

Although the foregoing embodiment has been aimed at the creation of bubbles as a contrast medium for ultrasonic diagnosis, the agent injected by the injecting device 1 may be the medicament for treatment. For example, a thrombus liquefacient such as urokinase is encapsulated together with the bubble-sourcing agent in microcapsules and distributed in a carrier liquid. After the encapsulated substance has been injected, the shock wave is applied to the position of blood vessel to be treated or the upstream position thereof, so that capsules are broken and the medicament is delivered only to the necessary portion.

Although the foregoing embodiment is the case of medical apparatus, the invention is also applicable to other industrial repairing apparatus by appropriately choosing the agents.

I claim:

1. An apparatus comprising:
   means for injecting into a blood vessel of a biotic body an agent including a plurality of particles having means for one of producing gas and providing medication encapsulated therein; and
   means for emitting a shock wave to a predetermined blood vessel in the biotic body with a pressure to effect breaking of the particles reaching the predetermined blood vessel so as to enable release of the means for one of producing gas and providing medication in the blood flowing in the predetermined blood vessel.

2. An apparatus according to claim 1, wherein the means for one of producing gas and providing medication is a gas producing means, and further comprising measuring means for emitting an ultrasonic wave to a desired position of the biotic body and for receiving waves reflected by bubbles created in the blood flow by the gas producing means in response to the breaking of the particles.

3. An apparatus according to claim 2, wherein the biotic body includes a heart providing a heart beat, and further comprising control means for controlling the shock wave emitting means to emit the shock wave in a predetermined phase relationship with the heart beat of the biotic body.

4. An apparatus according to claim 2, wherein the measuring means includes means for B-mode imaging.

5. An apparatus according to claim 2, wherein the measuring means includes doppler blood flow meter means for measuring speed of the blood flow based upon the doppler shift of the relected wave.

6. An apparatus according to claim 2, wherein the shock wave emitting means emits a shock wave with a dominant positive pressure.

7. An apparatus according to claim 1, further comprising cardiograph means for producing a cardiogram of the biotic body, timing control means for generating a trigger signal in a predetermined phase relationship with the cardiogram provided by the cardiograph means, and the shock wave emitting means being responsive to the timing control means for emitting the shock wave in response to the trigger signal.

8. An apparatus according to claim 7, wherein the means for one of producing gas and providing medication is a gas producing means, and further comprising measuring means for emitting an ultrasonic wave to a desired position of the biotic body and for receiving reflected by bubbles created in the blood flow by the gas producing means in response to the breaking of the particles.

9. An apparatus according to claim 8, wherein the timing control means generates the trigger signal at a timing which excludes an end portion of the diastolic period of the heart.

10. An apparatus according to claim 8, wherein the cardiograph means provides an electrocardiogram, and the timing control means includes means responsive to the cardiograph means for generating the trigger signal repeatedly upon expiration of a specified delay time following a specific wave on the electrocardiogram.

11. An apparatus according to claim 10, further comprising means for varying the setting of the delay time.

12. An apparatus according to claim 10, wherein the cardiograph means includes means for displaying the electrocardiogram and for displaying a time point of emission of the shock wave by the shock wave emitting means in relation with the electrocardiogram in accordance with the trigger signal generated by the timing control means.

13. An apparatus according to claim 12, wherein the displaying means displays the time point of emission of the shock wave on the waveform of the electrocardiogram.

14. An apparatus according to claim 8, wherein the timing control means controls the measuring means to inhibit measurement by the measuring means for a predetermined period.

15. An apparatus according to claim 11, wherein the means for one of producing gas and providing medication is a medication providing means.

16. A method comprising the steps of:
    injecting into a blood vessel of a biotic body an agent including a plurality of particles having means for one of producing gas and providing medication encapsulated therein; and
    emitting a shock wave to a predetermined blood vessel in the biotic body with a pressure sufficient to effect breaking of the particles reaching the predetermined blood vessel so that the means for one of producing gas and providing medication is released from the particles in blood flowing in the predetermined blood vessel.

17. A method according to claim 16, wherein the means for one of producing gas and providing medication is a gas producing means, and further comprising the steps of emitting an ultrasonic wave to a desired position of the biotic body and receiving a wave reflected by bubbles created in the blood flow by the gas producing means in response to the breaking of the particles.

18. A method according to claim 17, wherein the biotic body includes a heart providing a heart beat, and further comprising the steps of controlling a shock wave emitting means to emit the shock wave in a predetermined phase relationship with the heart beat of the biotic body.

19. A method according to claim 16, further comprising the steps of producing a cardiogram of the biotic body, generating a trigger signal in a predetermined phase relationship with the cardiogram and controlling the emission of the shock wave in accordance with the trigger signal.

20. A method according to claim 19, wherein the means for one of producing gas and providing medication is a gas producing means, and further comprising the steps emitting an ultrasonic wave to a desired position of the biotic body and receiving reflected by bubbles created in the blood flow by the gas producing means in response to the breaking of the particles.

21. A method according to claim 16, wherein the means for one of producing gas and providing medication is a medication providing means, and further comprising the step of treating the biotic body in accordance with the released medication.

* * * * *